United States Patent [19]

Yabe

[11] Patent Number: 4,809,680
[45] Date of Patent: Mar. 7, 1989

[54] ENDOSCOPE TIP

[75] Inventor: Hisao Yabe, Tokyo, Japan

[73] Assignee: Olympus Optical Co., Ltd., Tokyo, Japan

[21] Appl. No.: 90,071

[22] Filed: Aug. 27, 1987

[30] Foreign Application Priority Data

Sep. 1, 1986 [JP] Japan .................. 61-205682

[51] Int. Cl.⁴ .............................. A61B 1/06
[52] U.S. Cl. .............................. 128/6; 358/98
[58] Field of Search .............. 128/4, 6; 358/98

[56] References Cited

U.S. PATENT DOCUMENTS 4,573,450 3/1986 Arakawa .................. 128/6
4,646,721 3/1987 Arakawa .................. 128/6
4,692,608 9/1987 Cooper et al. ............ 128/6 X

FOREIGN PATENT DOCUMENTS 60-241011 11/1985 Japan .
60-184017 12/1985 Japan .

Primary Examiner—William H. Grieb
Attorney, Agent, or Firm—Armstrong, Nikaido, Marmelstein & Kubovcik

[57] ABSTRACT

In a rigid tip of an elongated insertable part, by an objective optical system of an optical axis parallel with the lengthwise axial direction of the tip, an image of an object to be imaged is to be formed in an image area of a solid state imaging device chip arranged so as to be parallel with the lengthwise axial direction through an optical device deflecting the optical axis of this objective optical system in a direction at right angles. Solid state imaging device chip bonding pads are provided only on the front end side and/or rear end side of this solid state imaging device chip.

34 Claims, 5 Drawing Sheets

ENDOSCOPE TIP

BACKGROUND OF THE INVENTION

Field of the Invention and Related Art Statement

This invention relates to an endoscope tip incorporating such solid state imaging device as a CCD.

There has come to be developed an endoscope wherein a solid state imaging device, such as a CCD (charge coupled device), is incorporated in the tip of the insertable part for observing the interior of a body cavity. An endoscope of this type such as shown, for example, in Japanese Utility model laid open No. 184017/1985 is suggested. In the formation of the tip of the insertable part of this endoscope, the optical axis of an objective is deflected at right angles by an optical device such as a prism and is led to the optical axis of a solid state imaging device provided in parallel with the lengthwise axial direction of the insertable part. The tip of the insertable part of the endoscope is made small in diameter by such a formation.

However, the arrangement of bonding pads and an optical black row of a solid state imaging device within the tip of the insertable part of the endoscope to make the tip smallest in diameter has not been investigated in a formation such as is mentioned above.

U.S. Pat. No. 4,573,450 is of a structure different relatively in the length part of the rigid tip fitting from the above mentioned prior art example, but is otherwise substantially the same and does not solve the above mentioned problem.

OBJECTS AND SUMMARY OF THE INVENTION

An object of the present invention is to provide an endoscope tip wherein a solid state imaging device is arranged substantially in parallel with the lengthwise direction to make the diameter of the tip small.

Another object of the present invention is to provide an endoscope wherein incorporated peripheral circuits can be easily connected.

According to the present invention, in the tip of an endoscope, wherein the image area surface of a solid state imaging device chip is arranged substantially in parallel with the lengthwise axial direction of the insertable part, bonding pads of a solid state imaging device chip are provided only in the front end and/or rear end part of the solid state imaging device chip with respect to the lengthwise axial direction of the insertable part to make the diameter of the tip small.

BRIEF DESCRIPTION OF THE DRAWINGS

FIG. 1 is a sectioned side view of a tip of an endoscope of the first embodiment.

FIG. 2 is a vertically sectioned view of the tip.

FIG. 3 is a top view of an incorporated solid state imaging device.

FIG. 4 is a front view of the tip.

DETAILED DESCRIPTION OF PREFERRED EMBODIMENTS

Figure 1:
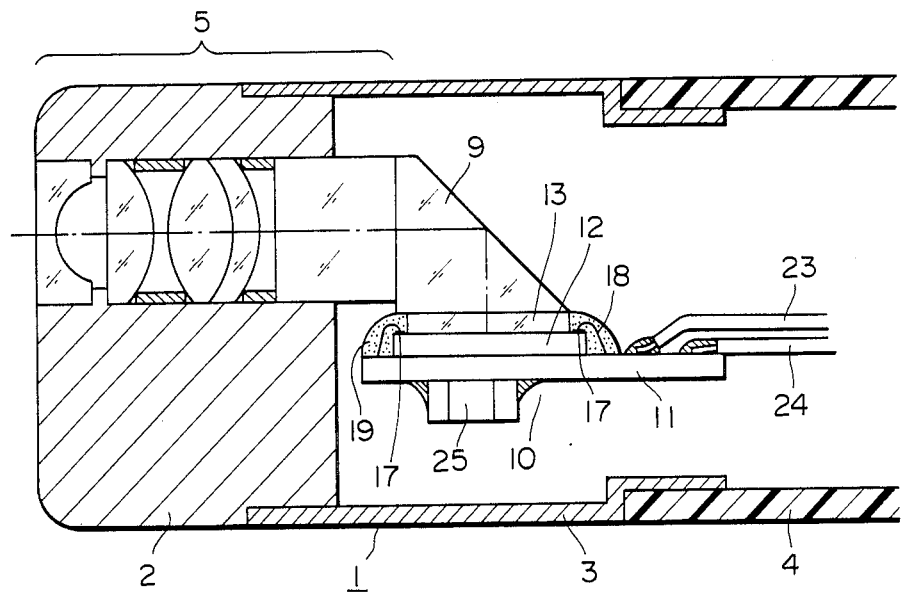
FIGS. 1 to 4 relate to the first embodiment of the present invention.
Figure 2:
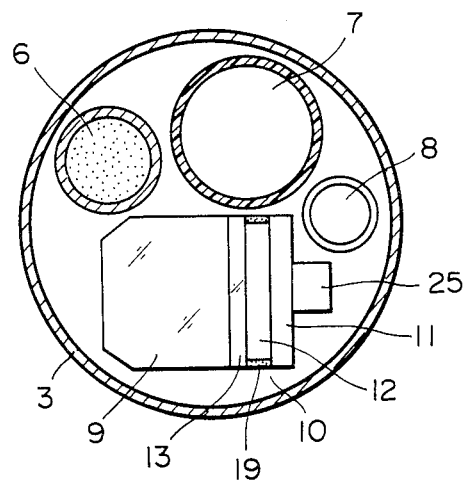

As shown in FIG. 1, a tip 1 of an insertable part of an endoscope is formed of a rigid tip forming member 2 such as of a metal. A cylindrical tip tube 3 is fitted at the front end of the tip forming member 2 and is fitted at the rear end to a flexible tube 4. An objective optical system 5 is provided as fixed in the tip forming member 2 so as to pass in the lengthwise direction through the tip of the insertable part of the endoscope. A light guide 6, forceps channel 7 and air and water feeding tube 8 shown in FIG. 2 are also provided to pass through the tip forming member 2. An optical device 9 consisting of a prism is provided in contact with the rear end of the objective optical system 5. An optical axis from the objective optical system 5 is deflected (reflexed) substantially at right angles with the optical device 9. A solid state imaging device 10 is provided in the optical axial direction deflected by the optical device 9. The solid state imaging device 10 is positioned substantially in parallel with the lengthwise direction of the tip 1 of the insertable part.

Figure 3:
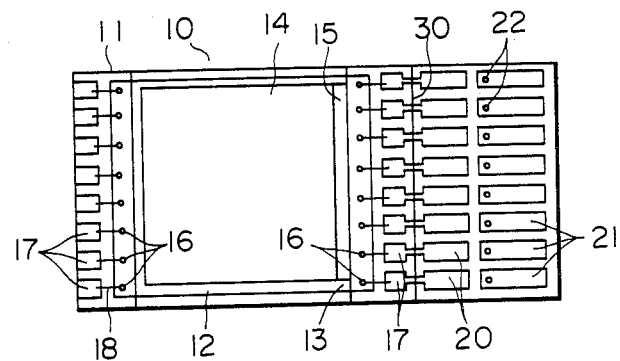

In the solid state imaging device 10, as shown in FIGS. 1 and 2, a CCD chip 12 is mounted on a ceramic base 11 and a cover glass 13 is fitted thereon. The upper surface of the cover glass is positioned so as to contact with the lower surface of the optical device 9. FIG. 3 is a view of the solid state imaging device 10 as seen from the cover glass 13 side (surface side). In FIG. 3, the left side is the distal side of the insertable part and the right side shows the proximal side. A square image area 14 is formed below the cover glass 13. A narrow band-like optical block row 15 is formed along the right side, that is, the proximal side end edge of the image area 14. Chip side bonding pads 16 are provided on the CCD chip at regular intervals along the distal side and proximal side end edges of the square CCD chip 12 as seen from the cover glass 13 side. Base side bonding pads 17 are so provided as to be arranged in parallel with the above mentioned chip side bonding pads 16 along the distal side and proximal side end edges of the CCD chip 12 on the ceramic base 11. These parallelly provided bonding pads 16 and 17 are electrically connected respectively with each other through bonding wires 18. These bonding pads 16 and 17 and bonding wires 18 are sealed with a sealing resin 19 as shown in FIG. 1.

The width of each of the optical device 9, cover glass 13 and ceramic base 11 is equal to or slightly larger than the width of the CCD chip 12. The CCD chip 12 is thinly covered on the side with the sealing resin 19. (In the other embodiments, too, the CCD chip is thinly covered with the sealing resin.)

For the thus formed solid state imaging device 10, the ceramic base 11 is formed as extending toward the proximal side in the lengthwise direction of the insertable part. Flat lands 20, extending in the lengthwise direction of the insertable part and connected with these base side bonding pads 17, are provided in parallel with the above mentioned base side bonding pads 17 on the proximal side. Further, flat lands 21, insulated from the flat lands 20 and extending in the lengthwise direction of the insertable part, are provided in parallel with the flat lands 20. Through holes 22, passing through the ceramic base 11, are formed in the flat lands 21 and are electrically connected with the base side bonding pads 17, on the distal side through a wiring pattern (not illustrated) provided on the back side of the ceramic base 11. That is to say, the wiring pattern, electrically connected with the bonding pads 17 on the distal side, is formed as wired also on the back surface side. In FIG. 3, the line represented by 30 respectively between the bonding pads 17 and the flat lands 20 shows the position of the end edge of the sealing resin 19. The conductive parts of signal lines 23 are connected by soldering to the flat lands 20 and the conductive parts of signal lines 24 are connected by soldering to the flat lands 21. Further, an electronic part 25 such as a condenser, is fitted by soldering to the back surface side of the ceramic base.

Thus, in this embodiment, the wiring pattern is formed on the ceramic base 11 and the electronic part or the like is fitted to it. Therefore, the ceramic base 11 itself performs the function of a substrate to be fitted on the lower surface side of a conventional ceramic base.

The above mentioned optical black row 15 is usually provided with about 20 picture elements in the width direction in a CCD. If the picture element size is 0.015×0.015 mm., the width of the optical black row 15 will reach 0.3 mm. which is a size not negligible in the formation of the tip of the insertable part of an endoscope and is a problem. In this embodiment, as the main optical black row 15 is adjacent to the image area 14 as shown in FIG. 3 and is provided on the proximal side (rear end side) in the lengthwise direction of the insertable part, such disadvantage as is mentioned above will not be produced. However, in case the main optical black row 15 is formed on the side adjacent to the image area 14 and parallel with the lengthwise direction of the insertable part (upper side or lower side in FIG. 3), the width in the diametral direction of the endoscope insertable part tip of the solid state imaging device 10 (the dimension in the vertical direction in FIGS. 2 and 3) will increase by 0.3 mm. Some optical black rows may be provided on the side parallel with the lengthwise direction of the insertable part.

Further, in the above mentioned embodiment, as shown in FIG. 2, the width of the solid state imaging device 10 and that of the optical device 9 are substantially the same and, as shown in FIG. 1, the proximal side end edge of the optical device 9 coincides with the proximal side end edge in the insertable part of the cover glass 13 of the solid state imaging device 10. Therefore, the solid state imaging device 10 and optical device 9 can be easily positioned relative to each other.

Also, in FIG. 2, the upward direction of the endoscope is the upward direction in the drawing and therefore the optical axis is deflected by the optical device 9 in the rightward and leftward directions with respect to the lengthwise direction of the insertable part. In such a case, the vertical direction of the optical image is not turned by the optical device 9 but the horizontal direction is turned. A horizontal shift register (not illustrated) is provided on the upper side of the image area 14 in FIG. 3, the vertical transfer direction is made leftward and therefore the vertical and horizontal directions in the image signal from the solid state imaging device 10 coincide respectively with those of the general TV camera.

The optical image can be made not to turn vertically and horizontally by using an even time reflecting prism as a dach prism such for the optical device 9. In such a case, preferably the horizontal transfer direction is made rightward in FIG. 3 and further the main optical black row 15 is provided on the left side of the image area 14.

Generally the horizontal shift register may be of a width of several picture elements, whereas the main optical black rows are required to be 20 rows (in the NTSC system) to 24 rows (in the PAL system). Therefore, as in the above mentioned embodiment, when the main optical black row is formed on the side intersecting at right angles with the lengthwise direction of the insertable part, the outside diameter of the insertable part of the endoscope can be made smaller. However, when an solid state imaging device, wherein the width of the horizontal shift register is larger than the width of the main optical black row (for example, in the case of parallelly reading out) is to be used, if the horizontal shift register is formed on the side intersecting at right angles with the lengthwise direction of the insertable part, the outside diameter of the tip of the endoscope can be made smaller. Thus, whichever is wider the main optical black row or the horizontal shift register, had better be provided on the side (distal side or proximal side) intersecting at right angles with the lengthwise direction of the insertable part.

Figure 4:
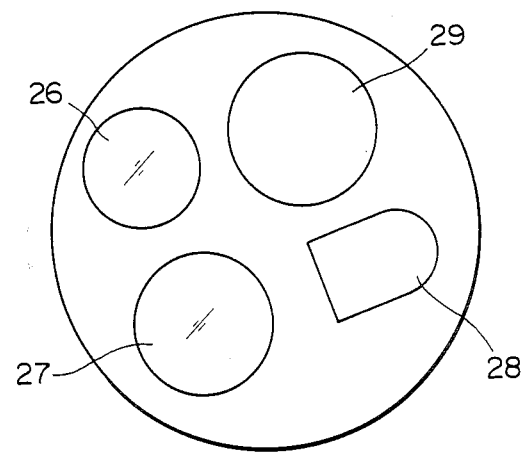

In the above mentioned embodiment, as shown in FIG. 2, the solid state imaging device 10, optical device 9 and objective optical system 5 are provided in the lower half (or upper half) of the insertable part tip, the forceps channel 7 and light guide 6 are provided in the upper half (or lower half) and the air and water feeding tube 8 is provided beside the solid state imaging device 10. An arrangement is considered to be an arrangement in which the insertable part tip can be made the smallest in diameter. In such a case, as shown in FIG. 4, an illuminating window 26 is adjacent to an observing window 27. In such a formation, when the insertable part tip approaches an object to be imaged, there will be obtained a picture in which there is little parallax of the illumination and the light is well distributed. The air and water feeding nozzle 28 is provided on the opposite side of the illuminating window 26 with the forceps port 29 between them. The air and water feeding nozzle 28 is thus provided in the position separate from the illuminating window 26 so that the illuminating light may not be obstructed by the air and water feeding nozzle 28.

In the above mentioned embodiment, the base side bonding pads 17 and chip side bonding pads 16 are provided on both of the distal side and proximal side in the lengthwise direction of the insertable part but may be provided only on one side, for example, the proximal side as required.

Figure 5:
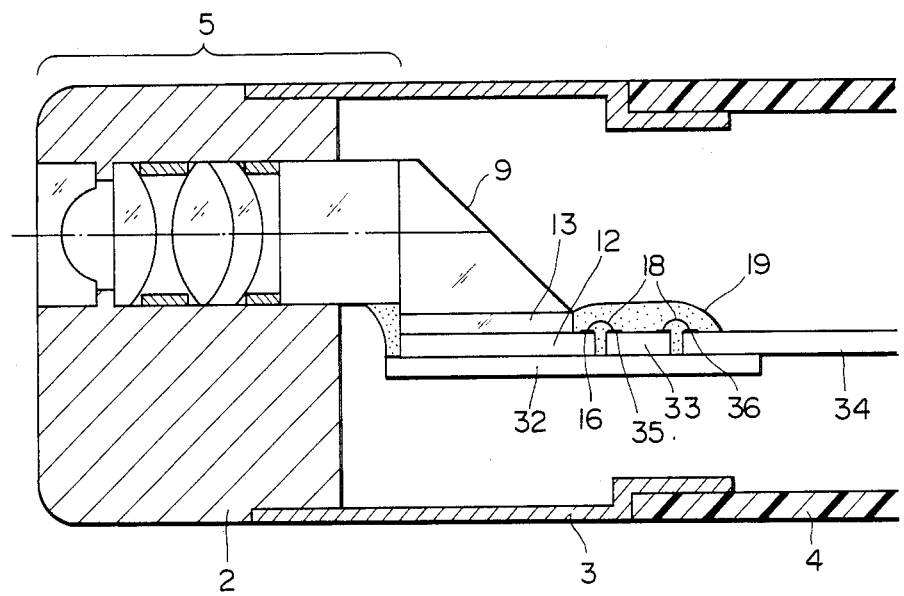
FIG. 5 is a sectioned side view of a tip of an endoscope of the second embodiment of the present invention.
Figure 6:
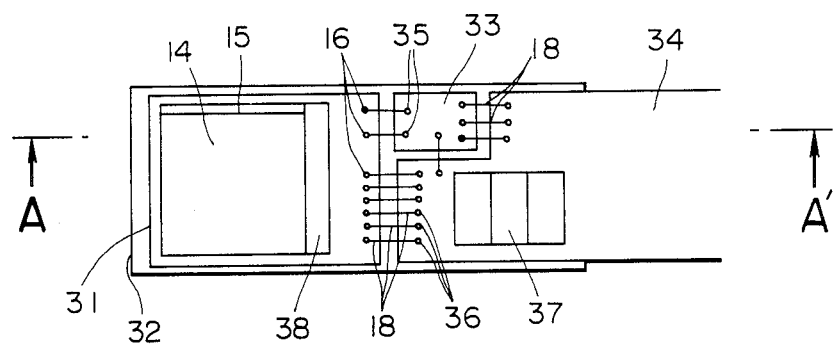
FIG. 6 is a top view showing a peripheral part fitted with a solid state imaging device chip in the second embodiment.

The second embodiment shall be explained in the following. In this second embodiment, as shown in FIG. 5 (showing the tip as sectioned on line A—A' in FIG. 6) and FIG. 6, a CCD chip 31 is die-bonded with a conductive paste to a base member 32 provided with no circuit pattern. In this case, the CCD chip 31 is fitted toward the front (which is the left in FIGS. 5 and 6) of the base member 32 which is formed of a metal plate. A peripheral IC chip 33 for amplifying and matching the video output signal is die-bonded with a conductive paste adjacently to the rear of the CCD chip 31. An FPC (flexible printed circuit) 34 is fitted on the front end side to the rear end of the paste. A GND terminal on the lower surface of the FPC 34 is conducted to the base member 32. For example, eight chip side bonding pads 16 of the above mentioned CCD chip 31 are provided only on the rear end edge side (not provided on the front end edge side) which is the proximal side of the CCD chip 31. Two of them are connected to the bonding pads 35 of the peripheral IC chip 33 and six of them are connected to the bonding pads 36 of the FPC 34. The bonding pads 35 on the side and at the rear end of the peripheral IC chip 33 are connected with the bonding pads 36 of the FPC 34 through the bonding wires 18.

A laminated ceramic condenser 37 is fitted to the FPC 34.

A square image area 14 is formed on the above mentioned CCD chip 31. A horizontal shift register 38 is formed along the rear end edge of the image area 14. The main optical black row 15 is formed along one side edge of the image area 14.

Figure 7:
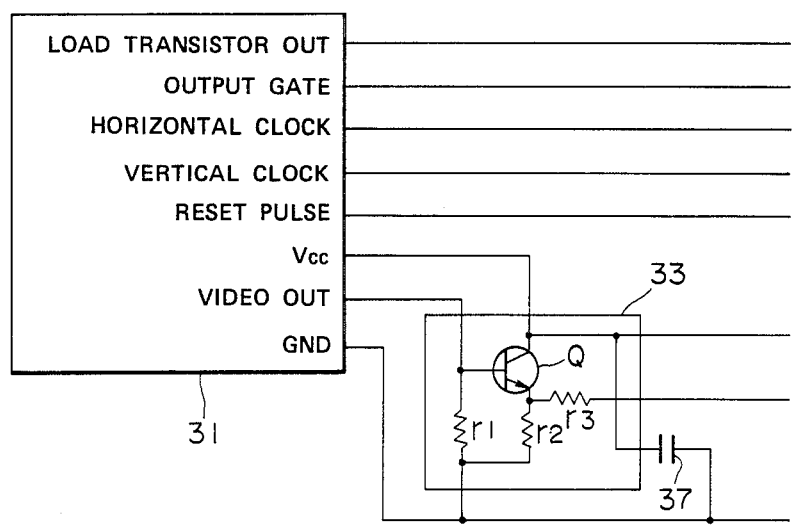
FIG. 7 is a circuit diagram showing an electric system of an imaging means contained in the tip of the endoscope of the second embodiment.

In case the above mentioned CCD chip 31 is connected through the bonding wires 18 or the like with the FPC 34 fitted with the peripheral IC chip 33 and condenser 37, a circuit such as is shown in FIG. 7 will be formed.

A video output signal will be applied to a matching resistance $r_1$ and also to the gate of a transistor Q and an amplified signal current will flow to a resistance $r_2$, of a small resistance value, on the emitter side. This signal will be input on the video processor side (not illustrated) through a video signal line $l_1$ with a matching resistance $r_3$ in series. A bypassing condenser 37 is connected between the collector of the transistor Q and GND to short-circuit at a high frequency the current source end of the CCD chip 31 with GND.

As shown in FIG. 5, the periphery of the part, connected through the above mentioned bonding wires 18, is sealed with a sealing resin 19 or the like.

The other structures are substantially the same as in the above mentioned first embodiment and are represented by the same reference numerals.

The second embodiment has the same advantages as the first embodiment, and is provided with the bonding pads 16 for the CCD chip 31 only on the proximal side with respect to the longitudinal axial direction of the endoscope so as to be compactly connected with the peripheral circuits and is therefore low in cost.

Also, in this embodiment, the base member 32 may be a mere metal plate having no circuit pattern so that the cost is.

Figure 8:
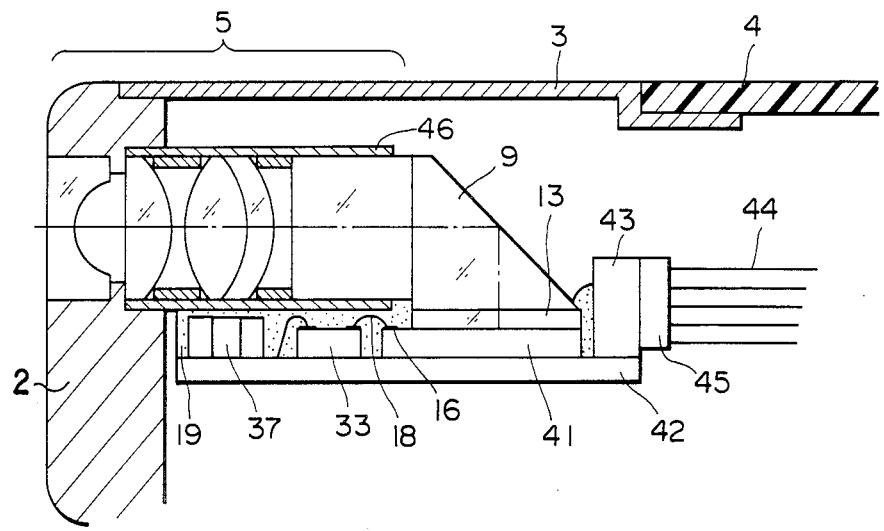
FIG. 8 is a sectioned side view of a tip of an endoscope of the third embodiment of the present invention.

FIG. 8 shows an essential part of the third embodiment of the present invention.

Which the bonding pads 16 are provided only on the rear end side in the above mentioned second embodiment, in the third embodiment, the bonding pads 16 are provided only on the front end side. The CCD chip 41 is die-bonded on the back surface in a rearward position on the upper surface of a substrate 42. The bonding pads 16, (only one is shown in FIG. 8) provided only on the front end side, are connected through the bonding wires 18 with bonding pads (not illustrated) provided integrally or separately on the peripheral IC chip 33 or the substrate 42.

The above mentioned substrate 42 is fitted with the peripheral IC chip 33 or laminated ceramic conderser 37. A connector receiver 43 is erected upward at the rear end of this substrare 42 so that a connector 45 of a signal cable 44 may be removably connected to the connector receiver 43.

This embodiment is connected with the objective optical system 5 after the wire bonding and is sealed with the sealing resin 19.

In this embodiment, the objective optical system 5 is fitted to the tip forming member 2 through a lens frame 46.

According to this embodiment, the same advantages as of the above mentioned second embodiment are obtained. When the peripheral IC chip 33 and laminated ceramic condenser 37, fitted to the substrate 42, are arranged on the outer peripheral part of the objective optical system 5, the fitting density is high and the length of the rigid part of the tip is short. Therefore, the pain to the patient, in case the insertable part is inserted into the body cavity, can be reduced.

Figure 9:
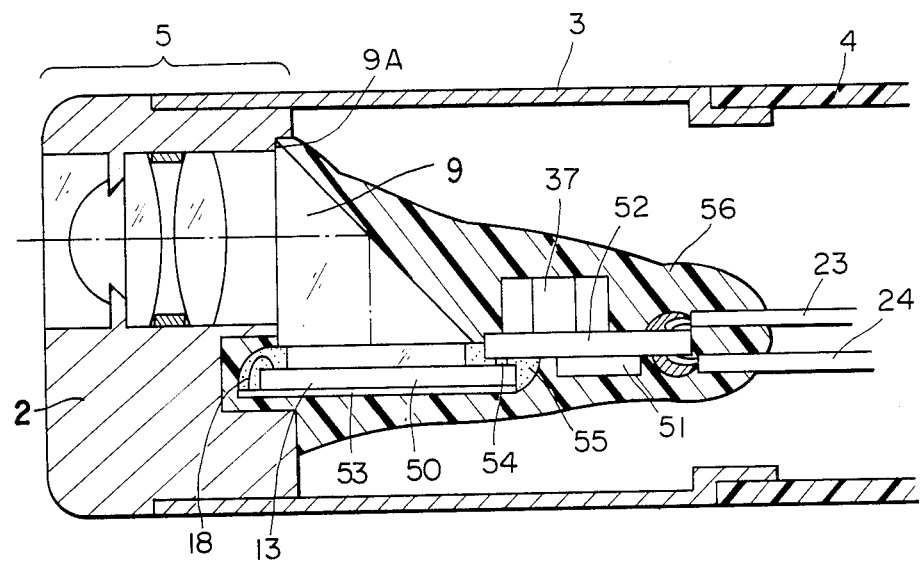
FIG. 9 is a sectioned side view of the fourth embodiment of the present invention.

FIG. 9 shows the fourth embodiment of the present invention. In this embodiment, a CCD chip 50 is face-bonded with a circuit substrate 52 fitted with such electronic part as the ceramic condenser 37 or a printing resistance 51 (or directly with the electronic part).

The tip forming member 2 is provided with a through hole so as to be fitted directly with the objective optical system 5 without a lens frame. At the exit end of the objective optical system 5, the optical device 9, by the prism changing the light path direction at right angles, is fixed with its front end side end surface peripheral edge part 9A and outer peripheral part in contact with a positioning recess formed on the rear end surface of the tip forming member 2. With both of these parts in contact with the recess, the optical device is positioned in the axial direction and diametral direction.

The image area surface of the CCD chip 50 is fitted in close contact with the exit end surface of the above mentioned optical device 9 through the cover glass 13. The CCD chip 50 is die-bonded on the back surface to a metal plate 53 so as to give a reference potential to the CCD chip 50 by the bonding wire on the tip side of the CCD chip 50.

Also, the CCD chip 50 is face-bonded on the rear end side with the circuit substrate 52 through a bump (projecting electrode) 54 provided in advance on the CCD chip 50 or circuit substrate 52 so as to be electrically connected.

The connecting part on the tip side of the CCD chip 50 by the above mentioned bonding wire 18, the face bonding part by the bump 54 on the rear end side of the CCD chip 50 and the side part of the CCD chip 50 are sealed with the first resin 55. The first resin 55 part on the side part of the CCD chip 50 is thin.

The above mentioned circuit substrate 52 and the CCD chip 50 and optical device 9 connected with the circuit substrate are sealed with the second resin 56 so as to reinforce the fixing of the respective parts and to prevent dampness.

The parts sealed with the above mentioned second resin 56 are contained in the tip tube 3 fixed at the front end on the outer periphery on the rear end side of the tip forming member 2. The flexible tube 4 is fixed at the front end to the rear end of the tip tube 3.

According to this embodiment, the CCD chip 50 and circuit substrate 52 can be overlapped with each other, the connecting part of the CCD chip 50 and circuit substrate 52 can be provided in the overlapped part and therefore the rigid tip forming part can be made shorter than in the embodiment using the wire bonding.

As another effect of the above described respective embodiments, the width of the circuit substrate (which is the ceramic substrate 11 in FIG. 1, the base member 32 in FIG. 5, the base member 32 and FPC 34 in FIG. 6, the substrate 42 in FIG. 8 and the circuit substrate 52 in FIG. 9) is substantially equal to or smaller than the width of the CCD chip and therefore the tip of the endoscope can be made small in diameter.

The tip of the straight sight type endoscope in which the observing direction (vision field direction) is directed in the forward direction of the axial direction of the insertable part is shown in the above described respective embodiments but this invention can be applied also to a side sight type endoscope in which the vision field direction intersects at right angles with the axial direction of the insertable part. In such a case, the optical axis of the objective optical system may be directed in the side sight direction intersecting at right angles with the above mentioned axial direction and the image area of the solid state imaging device chip may be arranged so as to be in the focal plane of the objective optical system without using the optical device 9.

In this invention, different embodiments can be formed by combining the above described respective embodiments.

What is claimed is:

1. An endoscope tip comprising:
   an image forming objective optical system arranged in a rigid tip member of an elongated insertable part so that an optical axis of the image forming objective optical system may be parallel with a lengthwise axial direction of said insertable part;
   an illuminating optical system being provided on a distal side of said elongated insertable part parallelly with said image forming objective optical system;
   an optical device being arranged on the optical axis of said image forming objective optical system, said optical device deflecting incident light at right angles;
   a solid state imaging device chip having a light receiving surface arranged opposed to an exit direction of the incident light from said optical device and to be substantially parallel with the lengthwise axial direction of said elongated insertable part;
   a base member connecting with said solid state imaging device chip;
   an electronic part being provided on said base member, near said solid state imaging device chip;
   signal cables connecting with a proximal side of said base member; and
   bonding pads being provided on said solid state imaging device chip only on the distal side and proximal side with respect to the direction parallel with the lengthwise axis of said elongated insertable part, said bonding pads to electrically connect at least one of said base member and said electronic part to the solid state imaging device chip.

2. An endoscope tip comprising:
   an image forming objective optical system arranged in a rigid tip member of an elongated insertable part so that an optical axis of the image forming objective optical system may be parallel with a lengthwise axial direction of said insertable part;
   an illuminating optical system being provided on a distal side of said elongated insertable part parallelly with said image forming objective optical system;
   an optical device being arranged on the optical axis of said image forming objective optical system, said optical device deflecting incident light at right angles;
   a solid state imaging device chip having a light receiving surface arranged opposed to an exit direction of the incident light from said optical device and to be substantially parallel with the lengthwise axial direction of said elongated insertable part;
   a base member connecting with said solid state imaging device chip;
   an electronic part being provided on said base member, near said solid state imaging device chip;
   signal cables connecting with a proximal side of said base member; and
   bonding pads being provided on said solid state imaging device chip only on the distal side with respect to the direction parallel with the lengthwise axis of said elongated insertable part, said bonding pads to electrically connect at least one of said base member and said electronic part to the solid state imaging device chip.

3. An endoscope tip comprising:
   an image forming objective optical system arranged in a rigid tip member of an elongated insertable part so that an optical axis of the image forming objective optical system may be parallel with a lengthwise axial direction of said insertable part;
   an illuminating optical system being provided on a distal side of said elongated insertable part parallelly with said image forming objective optical system;
   an optical device being arranged on the optical axis of said image forming objective optical system, said optical device deflecting incident light at right angles;
   a solid state imaging device chip having a light receiving surface arranged opposed to an exit direction of the incident light of said optical device and to be substantially parallel with the lengthwise axial direction of said elongated insertable part;
   a base member connecting with said solid state imaging device chip;
   an electronic part being provided on said base member near said solid state imaging device chip;
   signal cables connecting with a proximal side of said base member; and
   bonding pads being provided on said solid state imaging device chip only on the proximal side with respect to the direction parallel with the lengthwise axis of said elongated insertable part, said bonding pads to electrically connect at least one of said base member and said electronic part to the solid state imaging device chip.

4. An endoscope tip according to any of claims 1, 2 or 3 wherein said solid state imaging device chip has whichever is wider of a main optical black row and horizontal shift register provided on the distal side or proximal side in said lengthwise axial direction.

5. An endoscope tip according to any of claims 1, 2 or 3 wherein said solid state imaging device chip is die-bonded as deviated in a forward position of said base member.

6. An endoscope tip according to claim 2 or 3 wherein said solid state imaging device chip is die-bonded as deviated in a position toward a rear end of said base member.

7. An endoscope tip according to claim 5 wherein said base member has a peripheral IC chip fitted on a rear end side adjacent to said solid state imaging device chip.

8. An endoscope tip according to claim 5 wherein said base member is fitted with a peripheral IC chip on a surface on a side opposite a surface on which said solid state imaging device chip is fitted.

9. An endoscope tip according to claim 5 wherein said signal cables connect flat lands of said base member on a rear end side.

10. An endoscope tip according to claim 9 wherein said flat lands are provided in two rows in a direction intersecting at right angles with the lengthwise axial direction.

11. An endoscope tip according to claim 6 wherein said base member is fitted with a peripheral IC chip on a front side adjacent to said solid state imaging device chip.

12. An endoscope tip according to claim 6 wherein a connector, receiver, to be removably connected with a signal cable side connector is provided at the rear end of said base member.

13. An endoscope tip according to claim 7 wherein a flexible printed circuit plate is fitted on the rear end side of said base member adjacent to said solid state imaging device chip.

14. An endoscope tip according to claim 13 wherein said base member is formed of a metal plate.

15. An endoscope tip according to claim 14 wherein the bonding pads on said solid state imaging device chip are connected with said peripheral IC circuit and flexible printed circuit plate by wire bonding.

16. An endoscope tip according to any of claims 1, 2 or 3 wherein said solid state imaging device chip and said electronic part are electrically connected with each other by wire bonding.

17. An endoscope tip according to any of claims 1 or 3 wherein said solid state imaging device chip and said electronic part are electrically connected with each other by face bonding.

18. An endoscope tip according to any of claims 1, 2 or 3 wherein said electronic part is fitted to a back surface side of said base member.

19. An endoscope tip according to any of claims 1, 2 or 3 wherein a width of the base member fitted with said electronic part is substantially equal to or is smaller than a width of said solid state imaging device chip.

20. An endoscope tip according to any of claims 1, 2 or 3 wherein said solid state imaging device chip is thinly covered with a resin.

21. An endoscope tip according to any of claims 1, 2 or 3 wherein the width of each of said optical device and a cover glass is the same as or slightly larger than a width of said solid state imaging device chip.

22. An endoscope tip according to claims 1, 2 or 3, wherein said signal cables are connected in two columns on said base member, said columns being formed parallel to a side of the solid state imaging device chip which is in a vertical direction with the lengthwise axial direction of the elongated insertable part.

23. An endoscope tip according to claims 1, 2, or 3, wherein a width of the solid state imaging device chip in a vertical direction with respect to the lengthwise axial direction of the elongated insertable part and a width of the base member are either substantially equal or the width of the base member is slightly larger than the width of the solid state imaging device chip.

24. An endoscope tip according to claims 1, 2 or 3, wherein the light receiving surface of the solid state imaging device chip is fitted with a covered glass.

25. An endoscope tip according to claim 24, wherein a width of the optical device is the same as a width of the covered glass.

26. An endoscope tip according to claim 24, wherein edges of a distal side and proximal side of the optical device and the covered glass correspond.

27. An endoscope tip according to claim 24, wherein the edges of a distal side of said optical device and said covered glass correspond.

28. An endoscope tip according to claim 24, wherein the edges of a proximal side of said optical device and said covered glass correspond.

29. An endoscope tip comprising:
an image forming objective optical system arranged in a rigid tip member of an elongated insertable part so that an optical axis of the image forming objective optical system may be vertical with a lengthwise axial direction of said insertable part;
an illuminating optical system being provided on a distal side of said elongated insertable part parallelly with said image forming objective optical system;
a solid state imaging device chip having a light receiving surface arranged to be substantially parallel with the lengthwise axial direction of said elongated insertable part;
a base member connecting with said solid state imaging device chip;
an electronic part being provided on said base member near said solid state imaging device chip;
signal cables connecting with a proximal side of said base member; and
bonding pads being provided on said solid state imaging device chip only on the distal side and proximal side with respect to the lengthwise axial direction of said elongated insertable part, said bonding pads to electrically connect at least one of said base member and said electronic part to said solid state imaging device chip.

30. An endoscope tip comprising:
an image forming objective optical system arranged in a rigid tip member of an elongated insertable part so that an optical axis of the image forming objective optical system may be vertical with a lengthwise axial direction of said insertable part;
an illuminating optical system being provided on a distal side of said elongated insertable part parallelly with said image forming objective optical system;
a solid state imaging device chip having a light receiving surface arranged to be substantially parallel with the lengthwise axial direction of said elongated insertable part;
a base member connecting with said solid state imaging device chip;
an electronic part being provided on said base member near said solid state imaging device chip;
signal cables connecting with a proximal side of said base member; and
bonding pads being provided on said solid state imaging device chip only on the distal side with respect to the lengthwise axial direction of said elongated insertable part, said bonding pads to electrically connect at least one of said base member and said electronic part to said solid state imaging device chip.

31. An endoscope tip comprising:

an image forming objective optical system arranged in a rigid tip member of an elongated insertable part so that an optical axis of the image forming objective optical system may be vertical with a lengthwise axial direction of said insertable part;

an illuminating optical system being provided on a distal side of said elongated insertable part parallelly with said image forming objective optical system;

a solid state imaging device chip having a light receiving surface arranged to be substantially parallel with the lengthwise axial direction of said elongated insertable part;

a base member connecting with said solid state imaging device chip;

an electronic part being provided on said base member near said solid state imaging device chip;

signal cables connecting with a proximal side of said base member; and bonding pads being provided on said solid state imaging device chip only on the proximal side with respect to the lengthwise axial direction of said elongated insertable part, said bonding pads to electrically connect at least one of said base member and said electronic part to said solid state imaging device chip.

32. An endoscope tip according to claims 29, 30, or 31, wherein a covered glass is fitted to the light receiving surface of the solid state imaging device chip.

33. An endoscope tip according to claims 29, 30, or 31, wherein an optical black is provided on both a proximal side and a distal side of said solid state imaging device chip and said optical device is provided so that an image of the endoscope is an erect image.

34. An endoscope tip comprising:

an image forming objective optical system arranged in a rigid tip member of an elongated insertable part so that an optical axis of the image forming objective optical system may be parallel with a lengthwise axial direction of said insertable part;

an illuminating optical system being provided on a distal side of said elongated insertable part parallelly with said image forming objective optical system;

an optical device being arranged on the optical axis of said image forming objective optical system, said optical device deflecting incident light at right angles;

a solid state imaging device chip having a light receiving surface arranged opposed to an exit direction of the incident light of said optical device and to be substantially parallel with the lengthwise axial direction of said elongated insertable part;

a base member connecting with said solid state imaging device chip;

an electronic part being provided on said base member near said solid state imaging device chip;

signal cables connecting with a proximal side of said base member; and bonding pads being provided on said solid state imaging device chip only on the proximal side with respect to the direction parallel with the lengthwise axis of said elongated insertable part, said bonding pads to electrically connect said electronic part to the solid state imaging device chip;

wherein said electronic part is provided on a proximal side of said optical device, said electronic part being electrically connected with said solid state imaging device chip by wire bonding which is sealed by a resin, and the width of said electronic part being equal or smaller than a width of the solid state imaging device chip.

* * * * *